United States Patent [19]
Carson et al.

[11] Patent Number: 6,019,992
[45] Date of Patent: Feb. 1, 2000

[54] COSMETIC SKIN CARE COMPOSITIONS CONTAINING 4-CHROMANONE

[75] Inventors: Robert Carson, Rahway; Marieann Barratt, Palisades Park; Krupa Patel, Edison; Sreekumar Pillai, Wayne; Stewart Paton Granger, Paramus, all of N.J.

[73] Assignee: Chesebrough-Pond's USA Co., Greenwich, Conn.

[21] Appl. No.: 09/205,858

[22] Filed: Dec. 4, 1998

[51] Int. Cl.⁷ ..................................................... A61K 9/107
[52] U.S. Cl. .............................. 424/401; 514/938; 424/60
[58] Field of Search ..................... 424/401, 60; 514/456; 549/362

[56] References Cited

U.S. PATENT DOCUMENTS

| | | | |
|---|---|---|---|
| 3,864,484 | 2/1975 | Madaus | 424/195 |
| 4,065,574 | 12/1977 | Moon et al. | 424/283 |
| 5,276,061 | 1/1994 | DeLuca et al. | 514/844 |
| 5,434,186 | 7/1995 | Cohen et al. | 514/571 |

FOREIGN PATENT DOCUMENTS 55-111410  8/1980  Japan .

*Primary Examiner*—Thurman K. Page
*Assistant Examiner*—Alysia Berman
*Attorney, Agent, or Firm*—Rimma Mitelman

[57] ABSTRACT

Cosmetic skin care compositions containing 4-chromanone. The inventive compositions improve barrier function of the skin.

6 Claims, No Drawings

COSMETIC SKIN CARE COMPOSITIONS CONTAINING 4-CHROMANONE

FIELD OF THE INVENTION

Cosmetic compositions containing 4-chromanone, and methods of improving the cosmetic appearance of the skin by applying such compositions to the skin.

BACKGROUND OF THE INVENTION

The human skin consists of two major layers, the bottom thicker layer, dermis and the top thinner layer, the epidermis. Dermis is the layer which provides the strength, elasticity and the thickness to the skin. With aging, the thickness of the dermal layer is reduced and this is believed to be partially responsible for the formation of wrinkles in aging skin. The top layer of human skin or the epidermis which provides the resilience and the barrier properties of the skin, is composed of many different cell types. Keratinocytes are the major cell type of the epidermis (75–80% of the total number of cells in the human epidermis). Within the epidermis the keratinocytes reside in four distinct stages of differentiation. Epidermal differentiation is important for providing the essential function of the skin, namely to provide a protective barrier against the outside environment and to prevent loss of water from the body. Formation of the cornified envelope is the final stage of keratinocyte differentiation. The enzyme responsible for the formation of cornified envelopes, transglutaminase, is a marker of epidermal differentiation.

Another factor, in addition to skin thickness, imparts the barrier function to the skin. Layers of lipids in the skin form a "water barrier" which prevents water loss from the skin, and, consequently, the appearance of aged, dry or wrinkled skin. These lipids consist predominantly of ceramides, cholesterol, and fatty acids. In normal skin, if the barrier function is perturbed, the epidermis re-synthesizes the deficient lipids. Under certain conditions, however, a reduced capacity for re-synthesis may occur. This is especially so with aging or dry skin, where skin lipid levels are in any case sub-normal.

Agents which increase the thickness of the dermal layer and increase the lipid levels in the epidermal layer should therefore be ideal compounds for providing skin conditioning and anti-aging benefits.

In addition, sebum secretion decreases in post-menopausal women. Hormone replacement therapy elevates it toward pre-menopausal levels. Reduced sebum secretion in post-menopausal women may be associated with the skin dryness commonly noted in this group. Any material which enhances sebum production may provide a benefit to these women.

The present invention is based at least in part on the discoveries that the exposure of cultured keratinocytes to 4-chromanone results in the enhancement of differentiation and the expression of lipids essential to barrier function. 4-chromanone was also able to elevate sebum production in human sebocytes.

4-chromanone is a synthetic material, which is used as a starting material in syntheses of biologically active compounds. U.S. Pat. No. 3,864,484 (Madaus) mentions polyhydroxyphenyl chromanones for use in therapeutic compositions to protect from liver damage and inflammation. U.S. Pat. No. 4,065,574 (Moon et al.) mentions the use of 4-chromanone as a starting material for antifungal compounds but application to human skin is not disclosed. Japanese patent application 55111410 discloses the use of 3-Hydroxy-chromanone for skin lightening and sunburn prevention. 3-Hydroxy-chromanone is a tyrosinase inhibitor and uses 4-chromanone as a synthetic starting material.

SUMMARY OF THE INVENTION

The present invention includes a cosmetic skin care composition comprising:

(a) from 0.0001 to 30 wt. % of 4-chromanone of Formula I:

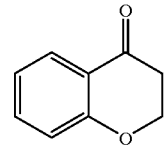

(b) a cosmetically acceptable vehicle.

Inventive compositions provide enhanced keratinocyte differentiation and enhanced lipid production and improved sebum secretion by sebocytes, which should result in improved barrier function and, consequently, reduced appearance of lines, wrinkles and aged skin, improved skin color, cosmetic treatment of dry or photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, legs, hands and scalp.

4-chromanone has the following structural formula:

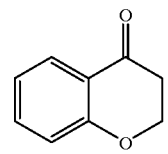

4-chromanone can be obtained from Sigma.

4-chromanone is incorporated in the inventive compositions in an amount of from 0.0001 to 30%, preferably in order to maximize benefits at a minimum cost, in an amount of from 0.001 to 20%, most preferably from 0.001 to 10%.

Cosmetically Acceptable Vehicle

The composition according to the invention also comprises a cosmetically acceptable vehicle to act as a dilutant, dispersant or carrier for 4-chromanone in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm$^2$/s (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Penetration of the stratum corneum would be essential for activity. Incorporation of 4-chromanone in a liquid formulation would greatly facilitate this penetration, as opposed to delivery from a powder. Thus, preferably, the vehicle is at least 80 wt. % water, by weight of the vehicle. Preferably, the amount of water is at least 50 wt. % of the inventive composition, most preferably from 60 to 80 wt. %, by weight of the composition.

Optional Skin Benefit Materials and Cosmetic Adjuncts

The inventive compositions preferably include sunscreens to lower skin's exposure to harmful UV rays.

Sunscreens include those materials commonly employed to block ultraviolet light. Illustrative compounds are the derivatives of PABA, cinnamate and derivatives of salicylate (other than ferulyl salicylate). For example, octyl methoxy-cinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507 (silicone-based anhydrous composition within a gelatine capsule), incorporated by reference herein. The invention accordingly also provides a closed container containing a cosmetically acceptable composition as herein defined.

The following specific examples further illustrate the invention, but the invention is not limited thereto.

EXAMPLES 1–4

Materials and Methods

Keratinocyte Culture

Normal human keratinocytes, isolated from neonatal foreskin by trypsin treatment, were grown in Dulbecco's Modified Eagle's Medium (DMEM, Life Technologies, Grand Island, New York) with 10% fetal bovine serum in the presence of irradiated mouse fibroblasts for establishing dividing keratinocyte colonies. Cells were incubated until their second passage and stored at –70° C. for future use. All incubations took place at 37 ° C. with 5% $CO_2$. Frozen second passage keratinocytes were thawed and plated in T-175 flasks (Corning, Corning, N.Y.) with DMEM and grown for five days. After reaching 80% confluence, they were trypsinized and seeded into 6-well plates containing keratinocyte growth medium (KGM, Clonetics, San Diego, Calif.) with 0.15 mM calcium.

Treatment of cells with 4-chromanone

Keratinocytes were plated in KGM (2 ml per well) at 0.2 million cells/plate in 6-well plates and grown for five days until the cells reached approximately 20% confluence. 4-chromanone was prepared fresh by dissolving in corn oil (100% Mazola Oil) as 2.5%, 5% or 10% w/vol. Cells were exposed to 4-chromanone by the addition of 10 µl of the corn oil chromanone mixture to 2 ml of medium in 6-well plates of keratinocyte. Treatment was started on day 5 by replacing the medium in the plates with two milliliters of fresh KGM and 10 µl of corn oil containing 0, 2.5, 5 or 10% 4-chromanone on the surface of the medium each day for three days. One set of triplicate wells was left untreated to serve as control.

Transglutaminase (TG-1) Assay

After three days of incubation, cells were washed thoroughly with phosphate buffered saline (PBS, 10 mM sodium phosphate, 138 mM sodium chloride, 2.7 mM potassium chloride, pH 7.4) and placed at -70 ° C. for 2 hours. Cells were then thawed for two hours. The DNA content of cells was quantified by using the DNA-binding fluorophore, bis-benzimidazole (Hoechst 33258) and measuring the specific fluoroescence of the DNA-bound fluorophore (360 nm excitation, 450 nm emission). Cellular TG-1 levels were determined by using a transglutaminase-1 (TG-1) specific monoclonal antibody as the primary antibody (BC1, Amersham, UK) and a peroxidase labeled rabbit antimouse IgG as the secondary antibody (Amersham, UK). The plates were blocked at room temperature with 5% nonfat milk in Tris-buffered saline (TBS, 10 mM Tris, 150 mM NaCL, pH 8.0) for one hour followed by two hours incubation with the primary antibody (1:4000 dilution) in 1% milk/TBS at room temperature. After rinsing the plates three times with 1% milk/TBS containing 0.05% Tween 20 (Bio-Rad, Hercules, Calif.), the plates were incubated with a 1:4000 dilution of the secondary antibody at room temperature for two hours. The plates were then rinsed three times with 1% milk/0.05% Tween 20/TBS and three times with PBS. Color was developed by incubation with o-phenylene-diamine (Sigma, St. Louis, Mo.) and hydrogen peroxide (Sigma) dissolved in a 1:1 mixture of 0.2 M dibasic sodium phosphate (Sigma) and 0.1 M citric acid at pH 5.0(Sigma). Solutions were transferred to 4 ml plastic cuvets (Fisher Scientific, Pittsburgh Pa.) and the absorbance was read at 492 nm on an Ultraspec 3000 spectrophotometer (Pharmacia, Piscataway N.J.) and TG-1 levels were expressed as absorbence/ DNA fluorescence.

Lipid Analysis

Keratinocytes were placed in KGM (2 ml per well) at 0.2 million per 6-well plates and grown for five days until approximately 20% confluence was reached. Cells were fed and treated with 4-chromanone as described above. After three days of treatment, cells were rinsed twice with PBS, then harvested by adding 3 ml of 0.1 N NaOH (Fisher) to each well and scraping with a rubber policeman. The supernatants were transferred to 16×100 mm glass test tubes with a teflon-coated caps and incubated for 1 hour at 70 ° C. After cooling to room temperature, a 50 µl aliquot was removed for protein determination (Pierce BCA assay, Rockford Ill.). To each tube 320 µl of 1 N HCl and 2.5 ml of chloroform were added and the tubes mixed well. The tubes were then placed on a tumbler and agitated for thirty minutes. The mixtures were then centrifuged for 10 minutes at 2000×g. Two milliliters of chloroform were removed from the organic phase and placed in an autosampler vial. The samples were then evaporated under $N_2$, resuspended in 60 µl of chloroform:methanol 2:1 and transferred to an autosampler insert microtube which was placed inside another autosampler vial which was sealed. Forty µl of the sample was spotted (Camag Automatic TLC Sampler III, Wilmington, N.C.) on silica TLC plates (Whatman 4807-700) and the plates were developed in horizontal chambers (Camag) using the following solvent system: 1. 95:4.5:0.5 chloroform, methanol, acetic acid and 2. 60:40:2 hexane, ethyl ether, acetic acid. Following immersion in 10% copper sulfate in 8% phosphoric acid, plates were charred at 165 ° C for 20 minutes and then read in a densitometer (Camag TLC Scanner II).

Experiments were conducted in which cultured keratinocytes were exposed to 4-chromanone in corn oil at 0, 2.5, 5 and 10% and incubated for three days with daily feeding and treatment. All transglutaminase expression was normalized to total cellular DNA and ceramide values were normalized to total cellular protein. Statistical differences were determined by using Student's t test and the JMP Statistical Discovery Software (SAS Institute) with p set at less than 0.05 as the level of significance Results that were obtained are summarized in Table 1.

TABLE 1

| EXAMPLE | MARKER | 4-CHROMANONE CONCENTRATION | % OF CONTROL | STD. DEV. (%) | P VALUE vs CONTROL | STATIST. SIGNIFIC. |
|---|---|---|---|---|---|---|
| 1 | TG-1 expression | 5% | 182 | 14 | <0.01 | YES |
|   | Ceramides | 5% | 131 | 4 | <0.05 | YES |
| 2 | TG-1 expression | 2.5% | 127 | 9 | >0.05 | NO |
|   |   | 5% | 295 | 2 | <0.05 | YES |
|   |   | 10% | 119 | 6 | >0.05 | NO |
|   | Ceramides | 2.5% | 123 | 15 | >0.05 | NO |
|   |   | 5% | 154 | 7 | <0.05 | YES |
|   |   | 10% | 75 | 40 | >0.05 | NO |
| 3 | TG-1 expression | 5% | 184 | 13 | <0.05 | YES |
|   |   | 10% | 162 | 3 | <0.05 | YES |
| 4 | Ceramides | 2.5% | 124 | 5 | >0.05 | NO |
|   |   | 5% | 123 | 21 | >0.05 | NO |
|   |   | 10% | 191 | 4 | <0.05 | YES |
|   | Cholesterol | 2.5% | 105 | 4 | >0.05 | NO |
|   |   | 5% | 124 | 8 | >0.05 | NO |
|   |   | 10% | 207 | 3 | <0.05 | YES |
|   | Fat Acids | 2.5% | 95 | 2 | >0.05 | NO |
|   |   | 5% | 113 | 20 | >0.05 | NO |
|   |   | 10% | 180 | 3 | <0.05 | YES |

It can be seen from the results in Table 1, that 4-chromanone was able to enhance differentiation and lipid production in cultured keratinocytes. Variation in cell response to different treatment concentrations of the active may be ascribed to normal biological variation between cell donors.

Thus, 4-chromanone delivered to growing keratinocytes altered cell functioning in ways that are associated with cosmetic benefit to the skin. Enhanced differentiation and lipid production should contribute to the formation of normal, integral skin barrier in conditions where it is compromised such as dry, lined, wrinkled, aged or photoaged skin and other conditions associated with impaired barrier function.

EXAMPLE 5

Human Sebocyte Culture

Human sebaceous glands were isolated from the nasal region of adult males (ages 60 and 75) and clonogenic sebocytes were cultured. Secondary cultures were harvested from mass culture (60% confluence) and subsequently passaged into 48 well paltes at a density of $1 \times 10^4$ cells/mm$^2$ surface area. Growth medium consisted of Clonetics Keratinocyte Basal Medium (KBM) supplemented with 14 $\mu$g/ml bovine pituitary extract (BPE, Clonetics), 0.4 $\mu$g/ml hydrocortisone (Sigma), 5 $\mu$ug/ml insulin (Sigam), 10 ng/ml Epidermal Growth Factor (EGF, Austral Biolgicals), 1.2× $10^{-10}$ M cholera toxin (ICN), 100 units/ml penicillin (Sigma), and 100 $\mu$g/ml streptomycin (Sigma). All cultures were incubated at 37° C in the presence of 7.5% $CO_2$. Under these conditions, a feeder layer of fibroblasts is not required. Sebocyte proliferation is comparable to that attained with serum-containing media. Medium (1 ml/well) was changed three times per week until cultures attained 3 days post-confluence growth (approximately 7 days).

$^{14}$C Acetate Incorporation into Human Sebocytes

On the day of experimentation, the growth medium was removed and the post-confluent sebocytes washed three times with sterile phosphate buffered saline (PBS). Fresh PBS in 0.5 ml amount was added to each well followed by 1–5 microliters of a test agent solubilized in 200 proof ethanol. Triplicate wells were used for each experimental cell. Controls consisted of distilled water and ethanol. Each plate was incubated for 24 hours at 37°C. in the presence of 7.5% $CO_2$. Radioactive label was prepared by adding 100 microliters of $^{14}$C-labeled acetic acid (Amersham, sodium salt, specific activity of 56 mCi/mmol) to 10 ml of 50 mM sodium acetate buffer. Then 50 microliters of labeled acetate was added to each well containing the sebocytes and test agents. The cultures were returned to the incubator for four hours. Thereafter, the sebocytes were rinsed three times with fresh PBS to remove unbound active and unbound radioactive label. Radioactive label remaining in the sebocytes was collected by harvesting the cells and counted using a Beckman scintillation counter. Duplicate aliquots were removed and assessed for total protein using the Pierce BCA assay. Test compounds were analyzed for statistical difference at the 95% confidence level using Students't test.

Cultured human sebocytes were exposed to 4-chromanone at 100, 50 and 10$\mu$M for 24 hours and then exposed to radiolabeled acetate for 4 hours. Acetate incorporation was measured as an indicator of lipid production. Results that were obtained are summarized in Table 2.

TABLE 2

| SAMPLE | ACETATE INCORPORATION. (%) | STANDARD DEVIATION (%) | P VALUE | STATISTICAL SIGNIFICANCE |
|---|---|---|---|---|
| CONTROL | 100 | 5 | — | — |
| 4-CHROMAN. 100 $\mu$M | 110 | 5 | >0.05 | NO |
| 4-CHROMAN. 50 $\mu$M | 114 | 4 | >0.05 | NO |
| 4-CHROMAN. 10 $\mu$M | 130 | 17 | <0.05 | YES |

4-Chromanone exhibited a reverse dose response with the 10$\mu$M treatment increasing lipid production by 30% in comparison to an untreated control. This difference was significantly different (see Table 2).

Thus, 4-Chromanone was also able to elevate sebum production in human sebocytes; such action may have beneficial effect on the cosmetic skin condition of post-menopausal women. Thus, a cosmetic method of improving sebum production by sebocytes in the skin of post-menopausal women is also a part of the present invention.

EXAMPLE 6

Example 6 illustrates topical compositions according to the present invention. The compositions can be processed in conventional manner. They are suitable for cosmetic use. In particular the compositions are suitable for application to wrinkled, rough, flaky, aged and/or UV-damaged skin and/or dry skin and post-menopausal skin to improve the appearance and the feel thereof as well as for application to healthy skin to prevent or retard deterioration thereof.

| OIL-IN-WATER EMULSION | |
|---|---|
| INGREDIENT | % w/w |
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| 4-chromanone | 2.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total | 100.00 |

OIL-IN-WATER EMULSION

| INGREDIENT | % w/w |
| --- | --- |
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| 4-chromanone | 2.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Propylparaben | 0.10 |
| Germall II | 0.10 |
| Fragrance | 0.10 |
| Total | 100.00 |

WATER-IN-OIL EMULSION

| INGREDIENT | % w/w |
| --- | --- |
| DI Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| 4-chromanone | 2.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total | 100.00 |

HYDRO-GEL

| INGREDIENT | % w/w |
| --- | --- |
| DI Water | 82.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| 4-chromanone | 2.00 |
| Methylparaben | 0.30 |
| Polysorbate 20 | 0.25 |
| Disodium EDTA | 0.10 |
| Germall II | 0.10 |
| Total | 100.00 |

ANHYDROUS SERUM

| INGREDIENT | % w/w |
| --- | --- |
| Cyclomethicone | 72.40 |
| 4-chromanone | 1.00 |
| Isopropyl Myristate | 5.00 |

-continued

ANHYDROUS SERUM

| INGREDIENT | % w/w |
| --- | --- |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total | 100.00 |

HYDRO-ALCOHOLIC GEL

| INGREDIENT | % w/w |
| --- | --- |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| 4-chromanone | 1.00 |
| Methylparaben | 0.30 |
| Polysorbate 20 | 0.25 |
| Disodium EDTA | 0.10 |
| Germall II | 0.10 |
| Total | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of treating aged, photoaged, dry, lined or wrinkled skin, the method comprising applying to the skin a cosmetic skin care composition comprising:

(a) from 0.0001 to 30 wt. % of 4-chromanone of Formula I:

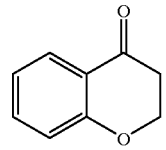

and (b) a cosmetically acceptable vehicle.

2. A cosmetic method of improving the barrier function of the skin, the method comprising applying to the skin a cosmetic skin care composition comprising:

(a) from 0.0001 to 30 wt. % of 4-chromanone of Formula I:

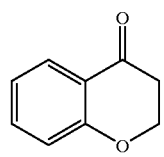

and (b) a cosmetically acceptable vehicle.

3. A cosmetic method of improving keratinocyte differentiation, the method comprising applying to the skin a cosmetic skin care composition comprising:

(a) from 0.0001 to 30 wt. % of 4-chromanone of Formula I:

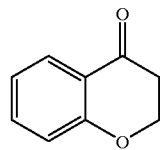

and (b) a cosmetically acceptable vehicle.

4. A cosmetic method of improving the lipid production by keratinocytes, the method comprising applying to the skin a cosmetic skin care composition comprising:

(a) from 0.0001 to 30 wt. % of 4-chromanone of Formula I:

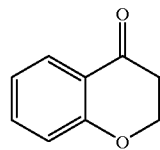

and (b) a cosmetically acceptable vehicle.

5. A cosmetic method of improving the sebum production by sebocytes, the method comprising applying to the skin a cosmetic skin care composition comprising:

(a) from 0.0001 to 30 wt. % of 4-chromanone of Formula I:

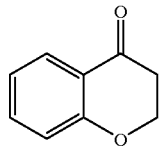

and (b) a cosmetically acceptable vehicle.

6. A cosmetic method of improving sebum production by sebocytes in the skin of post-menopausal women, the method comprising applying to the skin a cosmetic skin care composition comprising:

(a) from 0.0001 to 30 wt. % of 4-chromanone of Formula I:

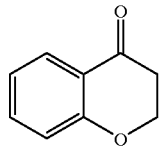

and (b) a cosmetically acceptable vehicle.

* * * * *